United States Patent [19]

Crosbie et al.

[11] Patent Number: 4,667,678

[45] Date of Patent: May 26, 1987

[54] ARTERIAL BLOOD VELOCITY TO VOLUME FLOW CONVERTER

[75] Inventors: Richard J. Crosbie, Langhorne, Pa.; Joseph Colombo, Rochester, N.Y.; J. Wallace Grant, Blacksburg, Va.

[73] Assignee: The United States of America as represented by the Secretary of the Navy, Washington, D.C.

[21] Appl. No.: 770,044

[22] Filed: Aug. 28, 1985

[51] Int. Cl.$^4$ .............................................. A61B 10/00
[52] U.S. Cl. .................................... 128/663; 128/667; 128/672; 128/713; 73/861.25
[58] Field of Search ................................ 128/661–663, 128/713, 667, 672, 692; 73/861.25

[56] References Cited

U.S. PATENT DOCUMENTS

| | | | |
|---|---|---|---|
| 3,498,290 | 3/1970 | Shaw et al. ........................ | 128/663 |
| 4,095,597 | 6/1978 | Hassler ............................... | 128/663 |
| 4,257,278 | 3/1981 | Papadofrangakis et al. . | |
| 4,336,808 | 6/1982 | Ohno et al. . | |
| 4,370,985 | 2/1983 | Takeichi et al. . | |
| 4,391,148 | 7/1983 | Sainz et al. . | |
| 4,493,216 | 1/1985 | Hassler . | |

FOREIGN PATENT DOCUMENTS 2389363  1/1979  France ................................. 128/663

OTHER PUBLICATIONS

Horton, "Blood Flow and Pressure Measurement", IBM Technical Disclosure Bulletin, vol. 13, No. 9, Feb. 1971, pp. 2471–2472.

*Primary Examiner*—Kyle L. Howell
*Assistant Examiner*—Ruth S. Smith
*Attorney, Agent, or Firm*—Robert F. Beers; Henry Hansen; James R. Burdett

[57] ABSTRACT

A arterial blood velocity-to-volume flow rate converter, including a pair of function generators a computer, and a multiplier, is incorporated within a system to objectively measure by non-invasive means the blood volume flow rate to the head of an occupant in a rapidly accelerating vehicle, and take corrective measures to stabilize the vehicle when that flow falls below a preselected lower limit for a predetermined length of time. A conventional ultrasonic Doppler velocimeter determines the blood velocity, subsequently feeding a representative signal to pressure function generator. The output therefrom is then fed to a cross-sectional area signal generator which determines the time-varying area of the artery, a signal representing such being fed to the multiplier along with the velocity signal to compute the flow. When that flow falls below a pre-selected lower limit for a predetermined length of time as determined by a comparator and timer, a command signal is sent to override circuitry to stablize the vehicle.

3 Claims, 3 Drawing Figures

ARTERIAL BLOOD VELOCITY TO VOLUME FLOW CONVERTER

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION

This invention relates generally to acceleration physiology, and more particularly to apparatus which can objectively measure by non-invasive means the arterial blood volumetric flow of a human in a rapidly accelerating vehicle.

Under acceleration, especially in the $+G_z$ or headward direction, a human will experience a wide variety of physiological changes among which is a reduction in perfusion blood pressure to the head area, particularly to the brain and eyes. Such a reduction occuring gradually results first in a loss of peripheral vision ("greyout"), followed by a complete loss of vision ("blackout"), and ultimately in a loss of consciousness. During rapid onset of acceleration, however, perfusion blood pressure to the head area is suddenly reduced resulting in a loss of consciousness without the typical "greyout" or "blackout" warning signals. This situation may occur, for example, to an occupant of a high performance aircraft capable of routinely exceeding 6 G's per second or in centrifuges which are specially adapted to produce centripetal accelerations with onset rates similar to in-flight environments.

Subjective endpoint criteria such as "greyout" and "blackout" have long been used in the evaluation of physiological anti-G devices. Nevertheless, because of the variability between test subjects with regard to experience, training, or motivation, and differences between testing facilities and testing criteria, such subjective measurements have generally been abandoned in favor of objective tests. On rare occasions, invasive pressure catheters have been utilized to measure arterial blood pressure response to acceleration. Due to the inherent danger for the human test subject involved and the compounding of these dangers by the acceleration, however, such invasive techniques are generally no longer used.

Perhaps the most popular device currently being used at centrifuge test facilities to objectively measure cardiovascular status during human acceleration stress studies is the transcutaneous, ultrasonic Doppler velocimeter. In most meters of this type, the Doppler frequency shift has been weighted using a power frequency technique so that it is proportional to the mean velocity. Examples of such meters and their use in acceleration physiology may be found in Rositano et al., "Non-Invasive Determination of Retrograde Eye-Level Blood Flow as a $G_z$ Tolerance Indicator, *Proceedings of the 44th Annual Scientific Meeting, Aerospace Medical Association,* Las Vegas, Nev., May 7-10, 1973.

Numerous methods which utilize such ultrasonic Doppler velocimeters have been proposed in the past for converting the blood velocity signals received thereby into the more useful blood volumetric flow information. With the majority of these techniques, however, it is assumed that the cross-sectional area of the blood vessel under examination remains constant throughout the cardic cycle. While such an assumption is considered valid for normal physiological conditions where the radius of an artery varies by only 7 to 10 percent, it becomes extremely restrictive under adverse conditions such as those experienced during acceleration stress where the decreasing pressures in arteries supplying the head can lead to reductions in the flow cross-sectional area of between 48 and 64 percent. Since the flow rate Q is equal to the product of mean arterial velocity V and the cross-sectional area A, significant errors in the calculated flow can be introduced under the constant cross-sectional area assumption.

SUMMARY OF THE INVENTION

Accordingly, it is a general purpose and object of the present invention to provide a non-invasive means of objectively measuring the arterial blood volumetric flow of an occupant in a rapidly accelerating vehicle such as a high performance aircraft. More specifically, it is an object of the present invention to accurately convert the arterial blood velocity data which is readily obtainable from conventional ultrasonic Doppler velocimeters into a more precise and useful blood volumetric flow information. Yet another object of the present invention is to provide apparatus which, when incorporated within a high performance aircraft or acceleration stress test facility such as a centrifuge, will continuously monitor the blood volumetric flow of an occupant in such a vehicle and take corrective action to stablize the vehicle when that flow is less than a predetermined lower limit for a predetermined length of time.

Briefly, these and other objects of the present invention are accomplished by a system having a velocimeter which utilizes the well-known ultrasonic Doppler method to non-invasively determine the velocity of blood within and along the axis of a selected artery in the head of an occupant of a rapidly accelerating vehicle. A signal that is indicative of the determined velocity is continuously fed to an arterial blood velocity-to-time flow converter, including a pair of function generators, a computer, and a multiplier. The velocity signal is first fed, along with a pair of preselected signals indicative of the occupant's at-rest diastolic blood pressure and velocity, into a pressure function generator which produces a time-varying signal indicative of the occupant's intra-arterial blood pressure, feeding it to a cross-sectional area signal generator. There, the pressure signal and a dimensionless ratio signal indicative of the ratio of the occupant's arterial wall thickness to his inner-arterial radius at zero pressure operate upon a function which produces a signal indicative of the time-varying cross-sectional area of the artery under determination. That signal, along with the velocity signal, is fed to a multiplier circuit, the output from which is displayed and fed to a comparator circuit representing the blood volume flow. When that flow falls below a preselected lower limit, fed as the second input to the comparator, for a predetermined length of time, a signal is fed to override circuitry which takes corrective action to stabilize the vehicle by deceleration until the occupant's blood volume flow returns to a level above the lower limit selected or until the occupant can himself regain control.

Other objects, advantages and novel features of the invention will become apparent from the following description of the preferred embodiment when considered in conjunction with the accompanying drawings wherein:

DESCRIPTION OF THE PREFERRED EMBODIMENT

Figure 1:
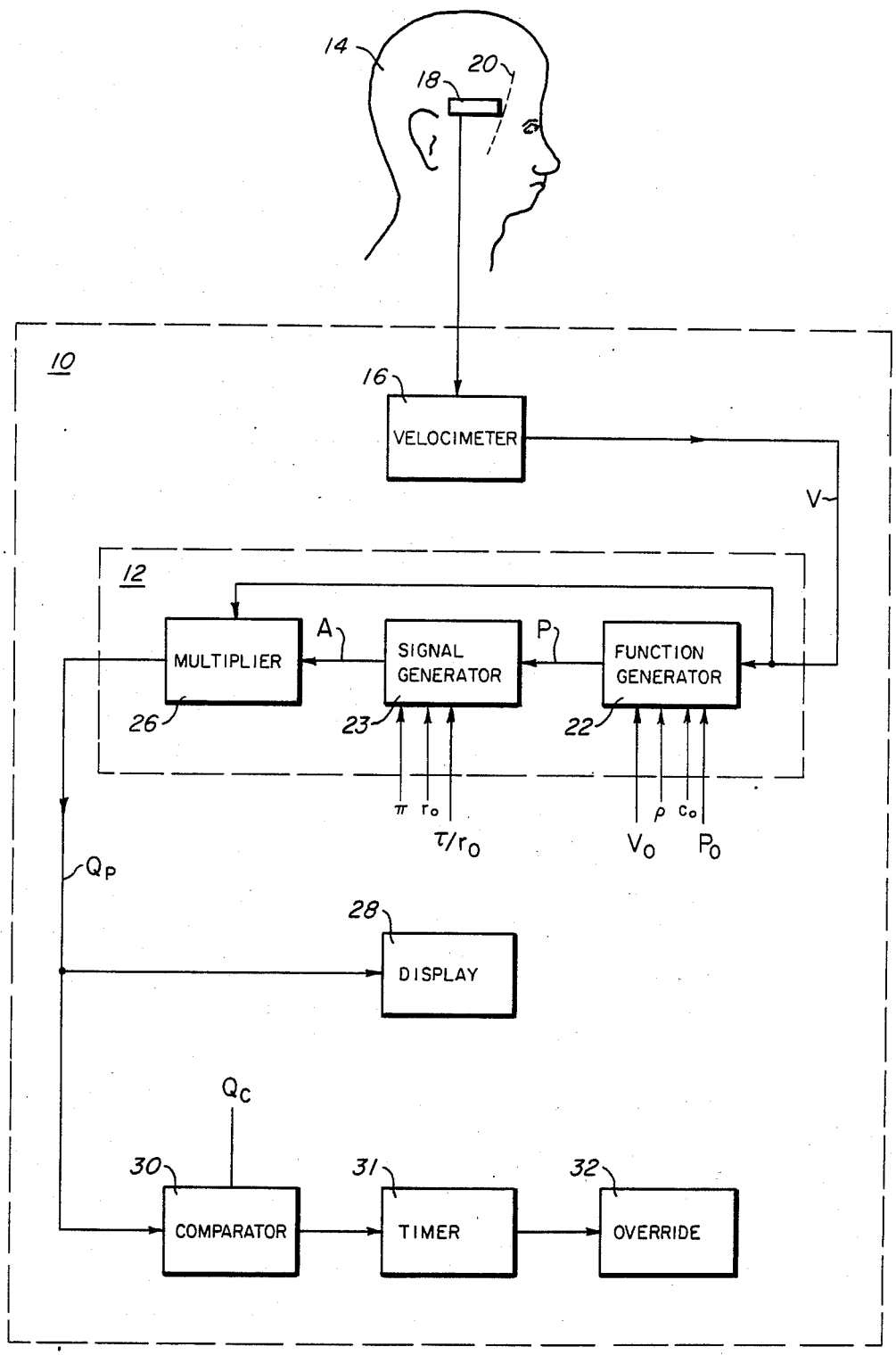
FIG. 1 illustrates the preferred embodiment of a system incorporating the arterial blood velocity-to-volume flow converter according to the present invention.

Referring now to the drawings, wherein like characters designate like or corresponding parts throughout the several views, there is shown in FIG. 1 the preferred embodiment of a system 10, including an arterial blood velocity-to-volume flow converter 12 according to the present invention, which may be used to monitor the arterial blood volume flow to the head of an occupant 14 in a rapidly accelerating vehicle (not shown) and which will take corrective action to stablize the vehicle when that flow is less than a predetermined lower limit for a predetermined length of time. The vehicle may be, for example, a high performance aircraft or any one of the dynamic flight simulators and centrifuges used in acceleration stress testing and evaluation.

As detailed herein above, it is well known that there is a direct correlation between a human test subject's blood velocity and his tolerance to the rapid onset of acceleration (see also Crosbie, R. J. "A Servo-Controlled Rapid Response Anti-G Valve", Report No. NADC-83087-60, Oct. 17, 1983, Government Accession No. AD A134-042). However, blood velocity as a measured value is not as useful as blood volume flow since a seemingly normal velocity reading under acceleration could, in actuality, be indicative of a reduction in flow due to a decrease in the cross-sectional area of the vessel monitored. The converter 12 is therefore used to accurately measure the intra-arterial blood pressure-dependent volume flow with the only continuously monitored parameter being the blood velocity.

A conventional ultrasonic Doppler velocimeter 16, such as the Model 1012 Directional Ultrasonic Flowmeter manufactured by L & M Electronics, Inc. of Daly City, Calif., is utilized in conjunction with its transducer or probe 18 to measure in a well-known manner the arterial blood velocity V of a suitable vessel such as the anterior superficial temporal artery 20 shown. The temporal artery 20 is selected in this preferred embodiment of the invention because it provides an easily obtainable measure of relative changes in retinal blood flow. Under acceleration, a drop in retinal blood flow results in a reduction of oxygen level in the retinal blood supply, a condition empirically associated with the loss of visual function. The frequency of the particular probe 18 chosen is dependent upon the depth of the vessel under consideration, for example a 9.3 MHz probe for shallow artery measurement. Moreover, the probe 18 is proximally positioned adjacent to the artery 20 in a conventional manner at an angle of approximately 45° and may be held in place, for example, by mounting it within a helmet (not shown) worn by occupant 14 so long as the probe 18 is essentially motionless and provides good contact with the skin.

Converter 12 includes a pressure function generator 22 and a cross-sectional area signal generator 23 initially loaded with data indicative of the occupant's at-rest status. Signals equivalent to the diastolic blood pressure (mm of Hg) and velocity $V_o$ (cm/sec) of the occupant 14 at rest, the mass density $\rho$ of whole blood, and the blood pressure wave speed $c_o$ (cm/sec) initialize the pressure function generator 22. Signals indicative of the inner-arterial radius $r_o$ (at zero pressure) and the arterial wall thickness $\tau$, both readily obtainable from a physiological handbook, initialize the area signal generator 23. Signal $\tau/r_o$ therefore represents the ratio of the occupant's arterial wall thickness to his inner arterial wall radius at zero pressure $r_o$. This ratio ranges from 0.1 to 0.2 for all real arteries, 0.2 being the value for small arteries such as the anterior superficial temproal artery 20 and 0.1 representative of large arteries such as the human aorta.

Having been initialized as such, the generation 22 is connected to receive the time-varying blood velocity signal V from the velocimeter 16, for generating a time-varying arterial blood pressure P in accordance with the function:

$$P = P_0 + \frac{\rho c_0 (v - v_0)}{1333.0} \qquad \text{Equation (1)}$$

Figure 2:
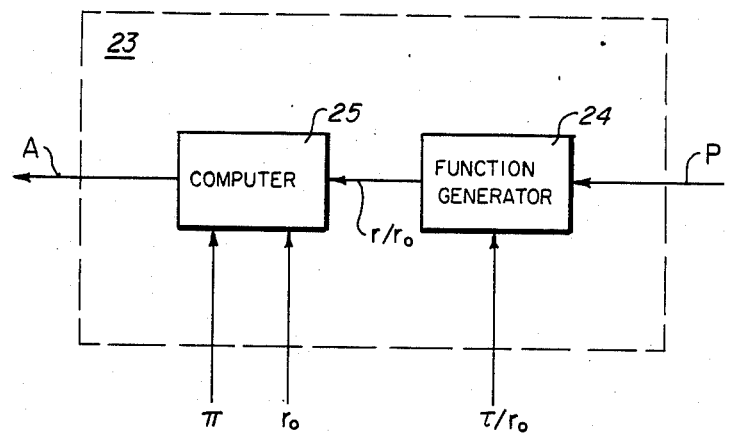
FIG. 2 shows in greater detail the cross-sectional area signal generator of FIG. 1.
Figure 3:
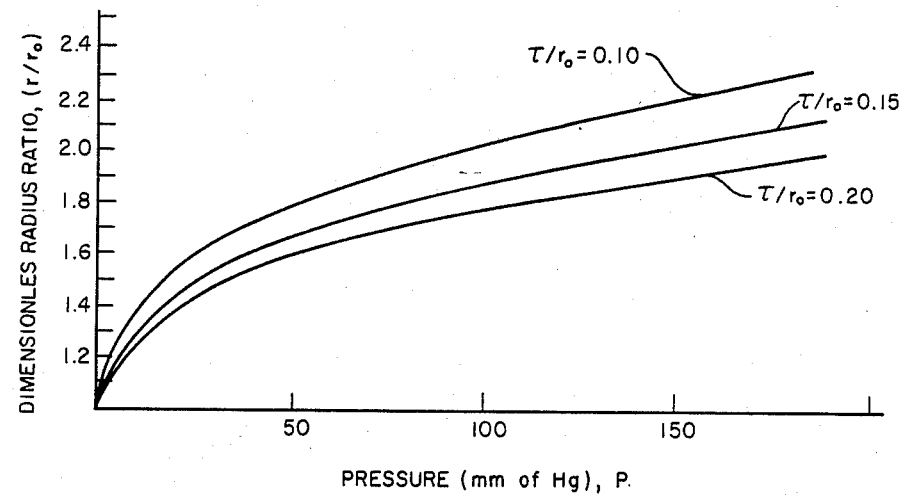
FIG. 3 shows a graphical representation of a cross-sectional area function generated in the converter of FIG. 1.

As shown in greater detail in FIG. 2, this time-varying signal P is fed to a second function generator 24 which, for a given value P and $\tau/r_o$, yields a particular value $r/r_o$, shown in FIG. 3. This signal $r/r_o$ is fed to a computer 25 where it is multiplied by the signal $r_o$ giving a value r which is squared and multiplied by the constant $\tau$ to yield the pressure dependent cross-sectional area signal A.

The function of FIG. 3 can be derived by numerically integrating the common differential relationship between pressure and radius in an artery. Wall stress $\sigma$ may be mathematically expressed both as a nonlinear function of strain deformation or extension ratio $r/r_o$ and as a function of the arterial pressure P. That is $$\sigma = K(\lambda - 1)^\gamma \qquad \text{Equation (2)}$$

where K and $\gamma$ are material constants from the stress-strain relationship $\sigma = K\epsilon^\gamma$ which depends on the location of the vessel within the arterial tree; and $$\sigma = \frac{1}{(\tau/r_0)} P\lambda \qquad \text{Equation (3)}$$

combining Equations (2) and (3), $$K(\lambda - 1) = \frac{1}{(\tau/r_0)} P\lambda, \qquad \text{Equation (4)}$$

then $$P\lambda = \frac{\tau}{r_0} K(\lambda - 1)^\gamma. \qquad \text{Equation (5)}$$

Differentiating $\lambda$ with respect to P yields $$P \frac{d\lambda}{dP} + \lambda = \left(\frac{\tau}{r_o}\right) K\gamma (\lambda - 1)^{\gamma - 1} \frac{d\lambda}{dP} \qquad \text{Equation (6)}$$

and transposing terms $$\frac{d\lambda}{dP} = \frac{\lambda}{\left(\frac{\tau}{r_o}\right) K\gamma(\lambda - 1)^{\gamma-1} - P} \quad \text{Equation (7)}$$

Since $\lambda = r/r_o$, then $$\frac{d\lambda}{d_p} = \frac{1}{r_0} \frac{dr}{d_p}.$$

These terms are then substituted in Equation (7) as follows $$\frac{dr}{dP} = \frac{r}{(\tau/r_o)K\gamma(\lambda - 1)^{\gamma-1} - P} \quad \text{Equation (8)}$$

Using a standard fourth order Runga-Kutta method, Equation (7) is numerically integrated to give $$r = \int \frac{rdP}{(\tau/r_o)K\gamma(\lambda - 1)^{\gamma-1} - P} \quad \text{Equation (9)}$$

and the cross-section area A, i.e. $\pi r^2$, is then $$A = \pi \left[ \int \frac{rdP}{(\tau/r_o)K\gamma\left(\frac{r}{r_o} - 1\right)^{\gamma-1} - P} \right]^2 \quad \text{Equation (10)}$$

where $r/r_o = \lambda$. The results of such an integration and, thus, the function to be generated by generator 24 is shown in FIG. 3. For a more detailed treatment of the material constants, see Tanaka et al., "Elastic and Inelastic Properties of the Canine Aorta and Their Variations Along the Aortic Tree", *J. Biomech.* Vol. 7, pp. 357–370 (1974).

Signal A is then fed to a multiplier 26 along with the velocity signal v where they are multiplied to yield a signal $Q_p$ which is indicative of the time-varying, pressure-dependent arterial blood volumetric flow. This signal $Q_p$ may be fed to a display 28, such as an analog device showing both the pulsatile and mean volumetric flow as well as the baseline or tolerable lower limit for each. In any case, signal $Q_p$ is fed to a comparator 30 and a timer 31 where it is compared to the lower limit $Q_c$, generating a command signal C which is set to system override circuitry 32 if the measured flow $Q_p$ is less than $Q_c$ for a predetermined length of time as determined by a timer 31. The override 32 may be as simple as power shut-down circuitry which could safely decelerate a centrifuge, or as complex as automatic pilot circuitry which could stabilize a high performance aircraft until such time as the pilot thereof can safely control it (i.e., when his arterial blood volume flow rate $Q_p$ exceeds the lower limit $Q_c$).

Some of the many advantages of the invention should now be readily apparent. For example, a non-invasive objective means of accurately measuring the arterial blood volumetric flow of the occupant in a rapidly accelerating vehicle is provided by a system which used a conventional ultrasonic Doppler flowmeter to measure in a well-known manner the arterial blood velocity of a selected artery. This velocity is fed to a converter including a pressure function generator, a cross-sectional area function generator, and a multiplier. With the mere introduction of a time-varying velocity signal, as well as several preselected constants, the converter produces a flow signal which is compared to a preselected lower limit in a comparator, ultimately producing a command signal to override circuitry when that flow falls below the lower limit for a predetermined length of time.

Obviously many modifications and variations of the present invention are possible in light of the above teachings. It is therefore to be understood that within the scope of the appended claims, the invention may be practiced otherwise than as specifically described.

What is claimed is:

1. Apparatus for measuring the volumetric flow of blood in an artery of a subject, comprising:
   velocimetric means formed to be non-invasively positioned adjacent to the artery for determining the speed of the blood within the artery, and for producing a first signal indicative thereof;
   first function generator means connected to receive said first signal for operating on signals initialized in said first function generator means indicative of diastolic blood pressure of the subject at rest, arterial blood velocity of the subject at rest, mass density of whole blood, and blood pressure wave speed, for producing a second signal indicative of the time-varying, intra-arterial blood pressure;
   second function generator means connected to receive said second signal for operating on signals initialized in said second function generator means indicative of inner-arterial radius at zero pressure, arterial wall thickness, and material constants from the stress-strain relationship $\sigma = K\epsilon^\gamma$, for producing a third signal indicative of the time varying, inner-arterial cross-sectional area as a function of blood pressure;
   multiplier means connected to receive said first and third signals for producing a fourth signal indicative of the volumetric flow of blood; and
   display means connected to said multiplier means for receiving the fourth signal for displaying a number indicative of the volumetric flow.

2. Apparatus according to claim 1, wherein said first function generator means further comprises:
   means for producing the second signal according to the function $$P = P_0 + \frac{\rho c_0(v - v_0)}{1333.0}$$

where $P_o$ is the signal indicative of the diastolic blood pressure, $\rho$ is the signal indicative of the mass density of whole blood, $c_o$ is the signal indicative of the blood pressure wave speed, v is said first signal and $v_o$ is the signal indicative of the diastolic blood velocity.

3. Apparatus according to claim 2, wherein said second function generator means further comprises:
   means for producing the third signal according to the function $$A = \pi \left[ \int \frac{rdP}{\left(\frac{\tau}{r_o}\right) K\gamma((r/r_o) - 1)^{\gamma-1} - P} \right]^2$$

where r is the inner-arterial radius, $\tau$ is the signal indicative of the arterial wall thickness, $r_o$ is the signal indicative of the inner-arterial radius at zero pressure, K and $\gamma$ are signals indicative of the material constants from the stress-strain relationship $\sigma = K\epsilon^\gamma$ and P is said second signal.

* * * * *